(12) United States Patent
Zhang et al.

(10) Patent No.: US 7,323,445 B2
(45) Date of Patent: *Jan. 29, 2008

(54) METHODS AND COMPOSITIONS FOR HEALING AND REPAIR OF ARTICULAR CARTILAGE

(75) Inventors: Renwen Zhang, Rutherford, NJ (US); Diane Peluso, Marshfield, MA (US); Elisabeth Morris, Sherborn, MA (US)

(73) Assignee: Genetics Institute, LLC, Cambridge, MA (US)

( * ) Notice: Subject to any disclaimer, the term of this patent is extended or adjusted under 35 U.S.C. 154(b) by 311 days.

This patent is subject to a terminal disclaimer.

(21) Appl. No.: 10/779,638

(22) Filed: Feb. 18, 2004

(65) Prior Publication Data

US 2004/0192605 A1 Sep. 30, 2004

Related U.S. Application Data

(63) Continuation of application No. 09/493,545, filed on Jan. 28, 2000, now Pat. No. 6,727,224.

(60) Provisional application No. 60/118,160, filed on Feb. 1, 1999.

(51) Int. Cl.
A61K 38/00 (2006.01)
(52) U.S. Cl. .............................. 514/12; 514/2; 514/12; 424/422; 424/423; 424/93.21; 424/93.7; 435/7.1; 435/320.1; 435/402
(58) Field of Classification Search ..................... None
See application file for complete search history.

(56) References Cited

U.S. PATENT DOCUMENTS

| | | | |
|---|---|---|---|
| 2,465,357 A | 3/1949 | Correll et al. |
| 3,955,719 A | 5/1976 | Pheulpin |
| 4,191,747 A | 3/1980 | Scheicher |
| 4,294,753 A | 10/1981 | Urist |
| 4,394,370 A | 7/1983 | Jeffries |
| 4,399,216 A | 8/1983 | Axel et al. |
| 4,419,446 A | 12/1983 | Howley et al. |
| 4,434,094 A | 2/1984 | Seyedin et al. |
| 4,441,915 A | 4/1984 | Arndt et al. |
| 4,455,256 A | 6/1984 | Urist |
| 4,468,464 A | 8/1984 | Cohen et al. |
| 4,472,840 A | 9/1984 | Jefferies |
| 4,553,542 A | 11/1985 | Schenk et al. |
| 4,563,350 A | 1/1986 | Nathan et al. |
| 4,596,574 A | 6/1986 | Urist |
| 4,608,199 A | 8/1986 | Caplan et al. |
| 4,619,989 A | 10/1986 | Urist |
| 4,627,982 A | 12/1986 | Seyedin et al. |
| 4,642,120 A | 2/1987 | Nevo et al. |
| 4,662,884 A | 5/1987 | Stenaas |
| 4,681,763 A | 7/1987 | Nathanson |
| 4,703,008 A | 10/1987 | Lin |
| 4,727,028 A | 2/1988 | Santerre et al. |
| 4,737,578 A | 4/1988 | Evans |
| 4,758,233 A | 7/1988 | Phillips et al. |
| 4,761,471 A | 8/1988 | Urist |
| 4,766,067 A | 8/1988 | Biswas et al. |
| 4,767,628 A | 8/1988 | Hutchinson |
| 4,769,328 A | 9/1988 | Murray et al. |
| 4,774,228 A | 9/1988 | Seyedin et al. |
| 4,774,322 A | 9/1988 | Seyedin et al. |
| 4,784,055 A | 11/1988 | Langen et al. |
| 4,789,732 A | 12/1988 | Urist |
| 4,795,804 A | 1/1989 | Urist |
| 4,798,885 A | 1/1989 | Mason |
| 4,804,744 A | 2/1989 | Sen |
| 4,810,691 A | 3/1989 | Seyedin |
| 4,828,990 A | 5/1989 | Higashi et al. |
| 4,843,063 A | 6/1989 | Seyedin |
| 4,851,521 A | 7/1989 | Della Valle et al. |
| 4,868,161 A | 9/1989 | Roberts |
| 4,877,864 A | 10/1989 | Wang et al. |
| 4,886,747 A | 12/1989 | Derynck |
| 4,908,204 A | 3/1990 | Robinson et al. |
| 4,920,962 A | 5/1990 | Proulx |
| 4,923,805 A | 5/1990 | Reddy et al. |
| 4,955,892 A | 9/1990 | Daniloff et al. |
| 4,963,146 A | 10/1990 | Li |
| 4,968,590 A | 11/1990 | Kuberasampath et al. |

(Continued)

FOREIGN PATENT DOCUMENTS

EP 0 052 510 5/1982

(Continued)

OTHER PUBLICATIONS

Henk et al. (Osteoarthritis and Cartilage, 1998, vol. 6, pp. 306-317).*

(Continued)

*Primary Examiner*—Hope Robinson
(74) *Attorney, Agent, or Firm*—Finnegan, Henderson, Farabow, Garrett & Dunner, L.L.P.

(57) ABSTRACT

Methods and compositions are provided for the treatment of articular cartilage defects and disease involving the combination of tissue, such as osteochondral grafts, with active growth factor. The active growth factor is preferably a composition containing at least one bone morphogenetic protein and a suitable carrier. The method results in the regeneration and/or functional repair of articular cartilage tissue.

18 Claims, No Drawings

U.S. PATENT DOCUMENTS

| | | | |
|---|---|---|---|
| 4,992,274 A | 2/1991 | Robinson et al. |
| 5,011,486 A | 4/1991 | Aebischer et al. |
| 5,011,691 A | 4/1991 | Oppermann |
| 5,013,649 A | 5/1991 | Wang et al. |
| 5,019,087 A | 5/1991 | Nichols |
| 5,024,841 A | 6/1991 | Chu et al. |
| 5,026,381 A | 6/1991 | Li |
| 5,041,538 A | 8/1991 | Ling et al. |
| 5,071,834 A | 12/1991 | Burton et al. |
| 5,089,396 A | 2/1992 | Mason et al. |
| 5,102,807 A | 4/1992 | Burger et al. |
| 5,106,626 A | 4/1992 | Parsons et al. |
| 5,106,748 A | 4/1992 | Wozney et al. |
| 5,108,753 A | 4/1992 | Kuberasampath |
| 5,108,922 A | 4/1992 | Wang et al. |
| 5,116,738 A | 5/1992 | Wang et al. |
| 5,118,667 A | 6/1992 | Adams et al. |
| 5,124,316 A | 6/1992 | Antoniades et al. |
| 5,141,905 A | 8/1992 | Rosen et al. |
| 5,147,399 A | 9/1992 | Dellon et al. |
| 5,166,058 A | 11/1992 | Wang et al. |
| 5,166,190 A | 11/1992 | Mather et al. |
| 5,166,322 A | 11/1992 | Shaw et al. |
| 5,168,050 A | 12/1992 | Hammonds |
| 5,171,579 A | 12/1992 | Ron et al. |
| 5,187,076 A | 2/1993 | Wozney et al. |
| 5,187,263 A | 2/1993 | Murray et al. |
| 5,202,120 A | 4/1993 | Silver et al. |
| 5,206,028 A | 4/1993 | Li |
| 5,208,219 A | 5/1993 | Ogawa et al. |
| 5,215,893 A | 6/1993 | Mason et al. |
| 5,216,126 A | 6/1993 | Cox et al. |
| 5,217,867 A | 6/1993 | Evans et al. |
| 5,218,090 A | 6/1993 | Connors |
| 5,229,495 A | 7/1993 | Ichijo et al. |
| 5,256,418 A | 10/1993 | Kemp et al. |
| 5,258,494 A | 11/1993 | Oppermann et al. |
| 5,266,683 A | 11/1993 | Oppermann et al. |
| 5,278,145 A | 1/1994 | Keller et al. |
| 5,284,756 A | 2/1994 | Grinna et al. |
| 5,286,654 A | 2/1994 | Cox et al. |
| 5,290,271 A | 3/1994 | Jernberg |
| 5,292,802 A | 3/1994 | Rhee et al. |
| 5,306,307 A | 4/1994 | Senter et al. |
| 5,308,889 A | 5/1994 | Rhee et al. |
| 5,324,519 A | 6/1994 | Dunn et al. |
| 5,324,775 A | 6/1994 | Rhee et al. |
| 5,328,955 A | 7/1994 | Rhee et al. |
| 5,352,715 A | 10/1994 | McMullin et al. |
| 5,354,557 A | 10/1994 | Oppermann et al. |
| 5,356,629 A | 10/1994 | Sander et al. |
| 5,364,839 A | 11/1994 | Gerhart et al. |
| 5,366,875 A | 11/1994 | Wozney et al. |
| 5,399,346 A | 3/1995 | Anderson et al. |
| 5,399,677 A | 3/1995 | Wolfman et al. |
| 5,405,390 A | 4/1995 | O'Leary et al. |
| 5,411,941 A | 5/1995 | Grinna et al. |
| 5,413,989 A | 5/1995 | Ogawa et al. |
| 5,420,243 A | 5/1995 | Ogawa et al. |
| 5,422,340 A | 6/1995 | Ammann et al. |
| 5,447,725 A | 9/1995 | Damiani et al. |
| 5,455,041 A | 10/1995 | Genco et al. |
| 5,455,329 A | 10/1995 | Wingender |
| 5,457,047 A | 10/1995 | Wingender |
| 5,457,092 A | 10/1995 | Schluter |
| 5,459,047 A | 10/1995 | Wozney et al. |
| 5,464,440 A | 11/1995 | Johansson |
| 5,508,263 A | 4/1996 | Grinna et al. |
| 5,516,654 A | 5/1996 | Israel |
| 5,520,923 A | 5/1996 | Tjia et al. |
| 5,538,892 A | 7/1996 | Donahoe et al. |
| 5,543,394 A | 8/1996 | Wozney et al. |
| 5,545,616 A | 8/1996 | Woddruff |
| 5,547,854 A | 8/1996 | Donahoe et al. |
| 5,556,767 A | 9/1996 | Rosen et al. |
| 5,618,924 A | 4/1997 | Wang et al. |
| 5,631,142 A | 5/1997 | Wang et al. |
| 5,635,372 A | 6/1997 | Celeste et al. |
| 5,635,373 A | 6/1997 | Wozney et al. |
| 5,637,480 A | 6/1997 | Celeste et al. |
| 5,639,638 A | 6/1997 | Wozney et al. |
| 5,645,592 A | 7/1997 | Nicolais et al. |
| 5,648,467 A | 7/1997 | Kobayashi et al. |
| 5,650,494 A | 7/1997 | Cerletti et al. |
| 5,658,882 A | 8/1997 | Celeste et al. |
| 5,661,007 A | 8/1997 | Wozney et al. |
| 5,674,292 A | 10/1997 | Tucker et al. |
| 5,688,678 A | 11/1997 | Hewick et al. |
| 5,693,779 A | 12/1997 | Moos, Jr. et al. |
| 5,700,664 A | 12/1997 | Bennett |
| 5,700,774 A | 12/1997 | Hattersley et al. |
| 5,700,911 A | 12/1997 | Wozney et al. |
| 5,703,043 A | 12/1997 | Celeste et al. |
| 5,728,679 A | 3/1998 | Celeste et al. |
| 5,750,651 A | 5/1998 | Opperman et al. |
| 5,752,974 A | 5/1998 | Rhee et al. |
| 5,756,457 A | 5/1998 | Wang et al. |
| 5,786,217 A | 7/1998 | Tubo et al. |
| 5,813,411 A | 9/1998 | Van Bladel etal. |
| 5,827,733 A | 10/1998 | Lee et al. |
| 5,842,477 A | 12/1998 | Naughton et al. |
| 5,846,931 A | 12/1998 | Hattersley et al. |
| 5,849,880 A | 12/1998 | Wozney et al. |
| 5,866,364 A | 2/1999 | Israel et al. |
| 5,932,216 A | 8/1999 | Celeste et al. |
| 5,935,594 A | 8/1999 | Ringeisen et al. |
| 5,936,067 A | 8/1999 | Graham et al. |
| 5,939,323 A | 8/1999 | Valentini et al. |
| 5,939,388 A | 8/1999 | Rosen et al. |
| 5,965,403 A | 10/1999 | Celeste et al. |
| 5,972,368 A | 10/1999 | MacKay |
| 5,986,058 A | 11/1999 | Lee et al. |
| 6,001,352 A | 12/1999 | Boyan et al. |
| 6,004,937 A | 12/1999 | Wood et al. |
| 6,027,919 A | 2/2000 | Celeste et al. |
| 6,034,061 A | 3/2000 | Rosen et al. |
| 6,034,062 A | 3/2000 | Thies et al. |
| 6,132,214 A | 10/2000 | Sohonen et al. |
| 6,150,328 A | 11/2000 | Wang et al. |
| 6,177,406 B1 | 1/2001 | Wang et al. |
| 6,187,742 B1 | 2/2001 | Wozney et al. |
| 6,190,880 B1 | 2/2001 | Israel et al. |
| 6,207,813 B1 | 3/2001 | Wozney et al. |
| 6,245,889 B1 | 6/2001 | Wang et al. |
| 6,284,872 B1 | 9/2001 | Celeste et al. |
| 6,287,816 B1 | 9/2001 | Rosen et al. |
| 6,291,206 B1 | 9/2001 | Wozney et al. |
| 6,331,612 B1 | 12/2001 | Celeste et al. |
| 6,340,668 B1 | 1/2002 | Celeste et al. |
| 6,432,919 B1 | 8/2002 | Wang et al. |
| 6,437,111 B1 | 8/2002 | Wozney et al. |
| 6,558,925 B2 | 5/2003 | Graham et al. |
| 6,586,388 B2 | 7/2003 | Oppermann et al. |
| 6,593,109 B1 | 7/2003 | Israel et al. |
| 6,610,513 B2 | 8/2003 | Wozney et al. |
| 6,613,744 B2 | 9/2003 | Wozney et al. |
| 6,623,934 B2 | 9/2003 | Celeste et al. |
| 6,699,471 B2 | 3/2004 | Radici et al. |
| 6,719,968 B2 | 4/2004 | Celeste et al. |

FOREIGN PATENT DOCUMENTS

| | | |
|---|---|---|
| EP | 0 058 481 | 8/1982 |
| EP | 0 121 976 | 10/1984 |

| | | |
|---|---|---|
| EP | 0 128 041 | 12/1984 |
| EP | 0 148 155 | 7/1985 |
| EP | 0 155476 | 9/1985 |
| EP | 0 169 016 | 1/1986 |
| EP | 0 177 343 | 4/1986 |
| EP | 0 222 491 | 10/1986 |
| EP | 0 212 474 | 3/1987 |
| EP | 0 241 809 | 10/1987 |
| EP | 0 336 760 | 4/1989 |
| EP | 0 329 239 | 8/1989 |
| EP | 0 394 418 | 10/1990 |
| EP | 0 401 055 | 12/1990 |
| EP | 0 409 472 | 1/1991 |
| EP | 0 416 578 | 3/1991 |
| EP | 0 429 570 | 6/1991 |
| EP | 0 433 225 | 6/1991 |
| EP | 0 512 844 | 11/1992 |
| EP | 0 530 804 | 3/1993 |
| EP | 0 531 448 | 11/1994 |
| EP | 0 626 451 | 11/1994 |
| EP | 0 688 869 | 12/1995 |
| EP | 0 831 884 | 5/1996 |
| EP | 0 313 578 | 8/1996 |
| EP | 0 741 187 | 11/1996 |
| EP | 0 592 562 | 1/1999 |
| EP | 1 061 940 | 2/1999 |
| EP | 0 536 186 | 11/2001 |
| EP | 1006957 | 11/2003 |
| JP | 63-181770 A | 7/1988 |
| JP | 05-123390 A2 | 5/1993 |
| JP | 03-345189 | 7/1993 |
| JP | 05-277174 A2 | 10/1993 |
| WO | WO 84/01106 | 3/1984 |
| WO | WO 85/04173 | 9/1985 |
| WO | WO 86/00525 | 1/1986 |
| WO | WO 86/00639 | 1/1986 |
| WO | WO 87/00528 | 1/1987 |
| WO | WO 88/00205 | 1/1988 |
| WO | WO 89/09787 | 10/1989 |
| WO | WO 89/09788 | 10/1989 |
| WO | WO 89/10133 | 11/1989 |
| WO | WO 89/10409 | 11/1989 |
| WO | WO 90/03733 | 4/1990 |
| WO | WO 90/11366 | 10/1990 |
| WO | WO 91/02744 | 3/1991 |
| WO | WO 91/04274 | 4/1991 |
| WO | WO 91/05802 | 5/1991 |
| WO | WO 91/10444 | 7/1991 |
| WO | WO 91/17777 | 11/1991 |
| WO | WO 91/18047 | 11/1991 |
| WO | WO 91/18098 | 11/1991 |
| WO | WO 92/05198 | 4/1992 |
| WO | WO 92/05199 | 4/1992 |
| WO | WO 92/07004 | 4/1992 |
| WO | WO 92/07073 | 4/1992 |
| WO | WO 92/14481 | 9/1992 |
| WO | WO 92/15323 | 9/1992 |
| WO | WO 92/09697 | 11/1992 |
| WO | WO 92/20793 | 11/1992 |
| WO | WO 92/22319 | 12/1992 |
| WO | WO 93/00049 | 1/1993 |
| WO | WO 93/00050 | 1/1993 |
| WO | WO 93/00432 | 1/1993 |
| WO | WO 93/04692 | 3/1993 |
| WO | WO 93/05751 | 4/1993 |
| WO | WO 93/06872 | 4/1993 |
| WO | WO 93/09228 | 5/1993 |
| WO | WO 93/09229 | 5/1993 |
| WO | WO 93/09802 | 5/1993 |
| WO | WO 93/13206 | 7/1993 |
| WO | WO 93/16099 | 8/1993 |
| WO | WO 93/19177 | 9/1993 |
| WO | WO 93/20858 | 10/1993 |
| WO | WO 94/01557 | 1/1994 |
| WO | WO 94/03200 | 2/1994 |
| WO | WO 94/06449 | 3/1994 |
| WO | WO 94/11502 | 5/1994 |
| WO | WO 94/15949 | 7/1994 |
| WO | WO 94/15965 | 7/1994 |
| WO | WO 94/15966 | 7/1994 |
| WO | WO 94/21681 | 9/1994 |
| WO | WO 94/24285 | 10/1994 |
| WO | WO 94/26892 | 11/1994 |
| WO | WO 94/26893 | 11/1994 |
| WO | WO 95/01801 | 1/1995 |
| WO | WO 95/01802 | 1/1995 |
| WO | WO 95/05846 | 3/1995 |
| WO | WO 95/07982 | 3/1995 |
| WO | WO 95/10539 | 4/1995 |
| WO | WO 95/10611 | 4/1995 |
| WO | WO 95/12664 | 5/1995 |
| WO | WO 95/15966 | 6/1995 |
| WO | WO 95/16035 | 6/1995 |
| WO | WO 95/33502 | 12/1995 |
| WO | WO 95/33830 | 12/1995 |
| WO | WO 96/01845 | 1/1996 |
| WO | WO 96/02559 | 2/1996 |
| WO | WO 96/14335 | 5/1996 |
| WO | WO 96/33215 | 10/1996 |
| WO | WO 96/36710 | 11/1996 |
| WO | WO 96/38570 | 12/1996 |
| WO | WO 96/39170 | 12/1996 |
| WO | WO 96/39203 | 12/1996 |
| WO | WO 96/40297 | 12/1996 |
| WO | WO 96/40883 | 12/1996 |
| WO | WO 97/15321 | 5/1997 |
| WO | WO 97/22308 | 6/1997 |
| WO | WO 97/34626 | 9/1997 |
| WO | WO 97/40137 | 10/1997 |
| WO | WO 97/45532 | 12/1997 |
| WO | WO 97/48275 | 12/1997 |
| WO | WO 97/49412 | 12/1997 |
| WO | WO 98/00183 | 1/1998 |
| WO | WO 98/16641 | 4/1998 |
| WO | WO 98/31788 | 7/1998 |
| WO | WO 98/34951 | 8/1998 |
| WO | WO 98/40113 | 9/1998 |
| WO | WO 98/49296 | 11/1998 |
| WO | WO 99/01159 | 1/1999 |
| WO | WO 99/24070 | 5/1999 |
| WO | WO 99/31120 | 6/1999 |
| WO | WO 99/37320 | 7/1999 |
| WO | WO 99/38543 | 8/1999 |
| WO | WO 99/45949 | 9/1999 |
| WO | WO 00/37124 | 6/2000 |
| WO | WO 00/43781 A | 7/2000 |

OTHER PUBLICATIONS

Outerbridge et al., JBJS, 1995, vol. 77, pp. 65-72.*
Aiba et al., *Blood*, 90:3923-3030 (1997).
Alberts et al., *Molecular Biology of the Cell*, Third Ed., Garland Publishing, Inc., New York, NY, pp. 1142 (1983).
Amizuka et al., *J. Cell Biol.*, 126:1611-1623 (1994).
Attisano et al., *Cell*, 68:97-108 (1992).
Baird et al., *Biochem. Biophys. Res. Comm.*, 138:476-482 (1986).
Barres. B.A. et al., *Development*, 118:283-295 (1993).
Basler, K. et al., *Cell*, 73:687-702 (1993).
Beck et al., *Growth Factors*, 2:273-282 (1990).
Belo et al., *Mech. Devel.*, 68:45-57 (1997).
Bendig, *Genetic Engineering*, 7:91-127 (1988).
Biben et al., *Develop. Biol.*, 194:135-151 (1998).
Bignami et al., *Brain Res.*, 43:429-435 (1972).
Bignami, A. et al., *Plasticity and Regeneration of the Nervous System*, 197-206 (1991).
Bolton et al., *Biochem J.*, 133:529 (1973).

Border et al., *J. Clin. Invest.*, 90:1-7 (1992).
Bouwmeester et al., *Nature*, 382:595-601 (1996).
Bowen-Pope et al., *J. Biol. Chem.*, 237:5161 (1982).
Bowie et al., *Science*, 247:1306-1310 (1990).
Brown et al., *J. Immunol.*, 142:679 (1989).
Broxmeyer et al., *PNAS*, 85:9052 (1988).
Bruder et al., *J. Cell Biochem.*, 56:283-294 (1994).
Burt, D.W., *BBRC*, 184:590-595 (1992).
Campoccia et al., *Biomaterials*, 19:2101-27 (1998).
Caplan, A., *Bone Repair and Regeneration*, 21:429-435 (1994).
Celeste et al., *J. Bone Mineral Res.*, 9:suppl. 5136 (1994).
Celeste et al., *PNAS*, 87:9843-9847 (1990).
Chang et al., *J. Biol. Chem.*, 269:28227-28234 (1994).
Conlon et al., *Development*, 120:1919 (1994).
Conlon et al., *Development*, 111:969 (1991).
Collignon et al., *Nature*, 381:155 (1996).
Creighton, T.E., *Proteins: Structure and Molecular Principles*, W.H. Freeman and Co., New York (1983).
Cunningham et al., *PNAS*, 89:11740-11744 (1992).
Dagert et al., *Gene*, 6:23 (1979).
Dale et al., *EMBO J.*, 12:4471 (1993).
D'Alessandro et al., *Growth Factors*, 11:53-69 (1994).
D'Allesandro et al., *J. Bone Mineral Res.*, (6) Suppl: 1:S153 (1991).
DeWulf et al., *Endocrinology*, 136:2652-2663 (1995).
Dexter et al., *Nature*, 344:380 (1990).
DiLeone et al., *Genetics*, 148:401-408 (1998).
Doctor et al., *Dev. Biol.*, 151:591-605 (1992).
Ducy et al., *Kidney Intl.*, 57:2207-2214 (2000).
Dunn et al., *Cancer Cells*, 3:227-234 (1985).
Ebner et al., *Science*, 260:1344-1348 (1993).
Estevez et al., *Nature*, 365:644-649 (1993).
Eto et al., *Biochem. Biophys. Res. Comm.*, 142:1095 (1987).
Fainsod et al, *Mech. Dev.*, 1:39-50 (1997).
Fallon et al., *J. Cell Biol.*, 100:198-207 (1985).
Fenton et al., *Endocrinology*, 129:1762-1768 (1991).
Finch et al., *PNAS*, 94:6770-6775 (1997).
Frishchauf et al., *J. Mol. Biol.*, 170:827-842 (1983).
Frommel et al., *J. Mol. Evol.*, 24:233-257 (1985.
Gamer et al., *Develop. Biol.*, 208:222-232 (1999).
Geisert et al., *Develop. Biol.*, 143:335-345 (1991).
Gerhart et al., *Trans. Othop. Res. Soc.*, 16:172 (1991).
Gething et al., *Nature*, 293:620-625 (1981).
Gitelman et al., *J. Cell. Biol.*, 126:1595-1609 (1994).
Goodman, R., *Methods for Serum-Free Culture of Neuronal and Lymphoid Cells*, 23-36 (1984).
Gough et al., *EMBO J.*, 4:645-653 (1985).
Graham et al., *EMBO*, 15:6505-6515 (1996).
Graham et al., *Growth Factors*, 7:151-160 (1992).
Graham et al., *J. Biol. Chem.*, 269:4974-4978 (1994).
Graham et al., *Nature*, 344:442 (1990).
Guigon et al., *Chem. Abstracts*, 96:36, Abstract No. 115633h (1982).
Guigon et al., *Cancer Res.*, 42:638 (1982).
Hammonds et al., *Mol. Endocrin.*, 5:149-155 (1991).
Harrison et al., *Exp. Cell Res.*, 92:340-345 (1991).
Hasimoto et al., *J. Biol. Chem.*, 267:7203-7206 (1992).
He et al., *Develop. Dynamics*, 196:133-142 (1993).
Hebda et al., *J. Invest. Dermatol.*, 91:440-445 (1988).
Hefti et al., *J. Neurobiol.*, 25:1418-1435 (1994).
Hemmati-Brinvanlou et al., *Nature*, 359:609-614 (1992).
Hoang et al., *J. Biol. Chem.*, 271:26131-26137 (1996).
Hollnagel et al., *Calcified Tissue Int'l*, 56:430 (1995).
Hunkapiller et al., *Meth. Enzymol.*, 91:399-413 (1983).
Inouye et al., *Mol. Cell. Endocrinol.*, 90:1 (1992).
Iwasaki, *J. Biol. Chem.*, 271:17360-5 (1996).
Janowska-Wieczorek et al., *Biol. Abstracts, Reviews-Reports-Meetings*, 33:61402 (1987).
Jonhagen et al., *Dement. Cogn. Disord.*, 9:246-257 (1998).
Joyce et al, *J. Cell Biochem.*, Suppl.17E:136, Abstract R504 (1993).
Kalyani et al., *J. Neuroscience*, 18: 7856-7869 (1998).
Karaplis et al., *Mol. Endocrin.*, 4:441-446 (1990).
Karaplis et al., *Genes & Development*, 8:277-289 (1994).
Katagiri et al., *J. Cell Biol.*, 127:1755-1766 (1994).

Kaufman et al., *Mol. Cell Biol.*, 2:1304-1319 (1982).
Kaufman et al., *Mol. Cell Biol.*, 5:1750-1759 (1985).
Kaufman et al., *J. Mol. Biol.*, 159:601-629 (1982).
Kaufman et al., *PNAS*, 82:689-693 (1985).
Kingsley et al., *Cell*, 71:399-410 (1992).
Kingsley et al., *Genes & Development*, 8:133-146 (1994).
Klein-Nulend et al., *Tissue Engineering*, 4:305-313 (1998).
Klein et al., *Brain Res.* 875:144-151 (2000).
Kliot et al., *Exper. Neur.*, 109:57-69 (1990).
Keonig et al., *Mol. Cell Biol.*, 14:5961-5974 (1994).
Koopman et al., *JBC*, 273:10103-10109 (1997).
Krueger, G.G., , *N. E. J. Med.*, 328:1845-1846 (1993).
LaPan et al., Program and Abstract, 13th Ann. Mtg of the AM Society of Bone and Min. Res., 8/24-28, p. 5153, Abstract No. 280, Mary Ann Liebert, Inc. NY (1991).
Lathe, J., *J. Mol. Biol.*, 183:1-12 (1985).
Lawn et al., *Cell*, 15:1157-1174 (1978).
Lefer et al., *PNAS*, 90:1018-22 (1993.
LeMaire et al., *Trends in Genetics*, 12:525-531 (1996).
Leslie M., *Nurse Practitioner*, 24:38, 41-8 (1999).
Lewin, *Science*, 237:1570 (1987).
Leyns et al., *Cell*, 88:747-756 (1997).
Lin et al., *Cell*, 68:775-785 (1992).
Lin et al., *Science*, 260:1130-1132 (1993).
Lipes et al., *PNAS*, 85:9704 (1988).
Lodish et al., *Mol. Cell Biol.*, 3rd Ed., W.H. Freeman & Co., p266 (1995).
Lopez-Coviella et al., *J. Physiol. Paris.*, 92:460-461 (1998).
Lopez-Coviella et al., *Science*, 289:313-316 (2000).
Lopez-Coviella et al., *Xth International Symposium on Cholinergic Mechanisms* (1998).
Lopez-Coviella et al., *Soc. Neurosci. Abstracts*, 25:517 (1999).
Lord et al., *Brit. J. Haematol.*, 34:441 (1976).
Lorimore et al., *Leuk. Res.*, 14:481-489 (1990).
Lowe et al., *Nature*, 381:158 (1996).
Lucas et al., *Differentiation*, 37:47-52 (1988).
Luthman et al., *Nucl. Acids Res.*, 11:1295-1308 (1983).
Luyten et al., *J. Biol. Chem.*, 264:13377-13380 (1989).
Luyten et al., *Exp. Cell. Res.*, 210(2):224-229 (1994).
Lyons et al., *PNAS*, 86:4554-4558 (1989).
Mangin et al., *PNAS*, 85:597-601 (1988).
Mangin et al., *Gene*, 95:195-202 (1990).
Maniatis et al., *Mol. Cloning, A Laboratory Manual, Cold Spring Harbor Laboratory, CSH*, N.Y.:310:323, 387-389 & 404-433 (1982).
Mantel et al., *PNAS*, 90:2232-2236 (1993).
Mansour et al., *J. Neurosci. Res.*, 25:300-377 (1990).
Marieb, E.N., *In Human Anatomy and Physiology*, 2nd Ed., The Benjamin/Cummings Publishing Co., pp. 373-375 (1992).
Mark, *J. Cell. Biol.*, 130:701-10 (1995).
Marra et al., *EMBL Database*, Accession No. AA120122 (1996).
Martin et al., *Crit. Rev. Biochem. Mol. Biol.*, 26:377-395 (1991).
Mason et al., *Nature*, 318:659-663 (1985).
Massague et al., *Trends in Cell Biol.*, 4:172-178 (1994).
Massague et al., *Cell*, 69:1067-1070 (1992).
Massague et al., *Cell*, 49:437-438 (1987).
Mathews et al., *Cell*, 65:973-982 (1991).
Matsuzaki et al., *J. Biol. Chem.*, 268:12719-12723 (1993).
Matzuk et al., *Nature*, 360:313 (1992).
McConahey et al., *Int. Arch. Allergy*, 29:185-189 (1966).
McDonald et al., *Cell*, 73:421-424 (1993).
Miller et al., *J. Immunol.*, 143:2907 (1989).
Miller et al., *Genetic Engineering*, 8:277-298 (1986).
Miyazono et al., *Gen Bank Record No. Z23154* (1993).
Morii et al., *J. Biol. Chem.*, 258:12749-12752 (1983).
Mullins et al., *Nature*, 303:856-858 (1984).
Nabeshima et al., *Alz Dis. And Assoc. Disord. 14(Suppl. 1)*:S39-S46 (2000).
Nakamura et al., *J. Biol. Chem.*, 267:18924-18928 (1992).
Nakao et al., *Mol. Cell Biol.*, 10:3646-3658 (1990).
Nakatani T., *Jap. J. Clin. Med.*, 52:824-33 (1994).
Nathan et al., *J. Cell Biol.*, 113:981-986 (1991).
Neuhaus et al., *Mech. Dev.*, 80:181-184 (1999).

Nirschl, R., *American Orthopaedic Society for Sports Medicine*, Leadbetter, W. et al., eds, Ch. 13:577-585 (1989).
Ngo et al., *Merz et al., eds., Brickhauser, Boston*, Springer Verlag, pp. 433-434 & 492-495 (1994).
Noble et al., *J. Neuroscience*, 4:1892-1903 (1984).
Obaru et al., *J. Biochem.*, 99:885 (1986).
Ogawa et al., *J. Biol. Chem.*, 267:14233 (1992).
Ohura et al., *J. Biomed. Mat. Res.*, 30:193-200 (1996).
Ohura et al., *J. Biomed. Mat. Res.*, 44: 168-175 (1999).
Okayama et al., *Mol. Cell Biol.*, 2:161-170 (1982).
Ozkaynak et al., *EMBO Journal*, 9:2085-2093 (1990).
Padgett et al., *Nature*, 325:81-84 (1987).
Paralkar, et al., *J. Cell Biol.*, 119:1721-1728 (1992).
Park et al., *J. Biol. Chem.*, 271:8161-9 (1996).
Patel et al., Pharmacotherapy of Cognitive Impairment in Alzheimer's Disease: A Review:81-95 (1992).
Perides et al., *J. Biol. Chem.*, 269:765-770 (1994).
Perides et al., *PNAS*, 89:10326-10330 (1992).
Peyron, J.G. *J. Rheumatol. Suppl.*, 27:2-3 (1991).
Pierce et al., *J. Clin. Investig.*, 96:1336-50 (1995).
Pollock, *J. Biol. Chem.*, 271:8008-14 (1996).
Pragnell et al., *Blood*, 72:196-201 (1988).
2001-2002 Progress Report on Alzheimer's Disease, *National Institute on Aging; NIH*:1-51 (2002).
Rabin et al., *Mol. Cell. Biol.*, 13:2203-2213 (1993).
Ralph et al., *Cancer Res.*, 37:546 (1977).
Ralph et al., *J. Immunol.*, 114:898 (1975).
Rattner et al., *PNAS*, 94:2859-2863 (1997).
Reddi, A. *JBJS*, 83-A:S1-1:S1-S6 (2001).
Reddi et al., *Osteoporosis, Academic Press*, pp. 281-287 (1996).
Reddi et al., *PNAS*, 69:1601 (1972).
Reeck, *Cell*, 50:667 (1987).
Roberts et al., *PNAS*, 83:4167-4171 (1986).
Robertson et al., *Biochem. Biophys. Res. Commun.*, 149:744-749 (1987).
Rodeo et al., *Orthopaedic Res. Soc.*, 41st Annual Mtg, Orlando, Florida, p. 288 (1995).
Rodeo, et al., *J. Bone Joint Surg.*, 75-A:1795-1803 (1993).
Rosen et al., *Trends in Genetics*, 8:97-102 (1992).
Rosen et al., *Connect Tissue Res.*, 20:313-9 (1989).
Rubin et al., *Science*, 287:2204-2215 (2000).
Rudinger, *Peptide Hormones*, Parsons (ed.), U Park Press, Baltimore:1-7 (1976).
Sakai et al., *PNAS*, 87:8378-8382 (1990).
Salic et al., *Development*, 124:4739-4748 (1997).
Sambrook et al., *Mol. Cloning: A Laboratory Manual*, 2nd Ed., vol. 1, 2 and 3, Cold Spring Harbor Laboratory Press: Cold Spring Harbor, New York, USA (1989).
Sampath et al., *J. Biol Chem.*, 267:20352-20362 (1992).
Sampath et al., *J. Biol Chem.*, 265:13198-13205 (1990).
Sampath et al., *PNAS*, 84:7109-7113 (1987).
Sampath et al., *PNAS*, 80:6591-6595 (1983).
Sampath et al., *Exp. Cell. Res.*, 143:460-64 (1982).
Sato et al., *Clin. Orthopaedics Related Res.*, 183:180-187 (1984).
Saukkonon et al., *J. Exp. Med.*, 171:439 (1990).
Schubert et al., *Nature*, 344:868-870 (1990).
Schulz et al., *Principles of Protein Structure*, Springer-Verlag New York, Inc., New York:14-16 (1979).
Shah, et al., *J. Cell Sci.*, 108:985-1002 (1995).
Shimasaki et al., *PNAS*, 85:4218-4222 (1988).
Shipley et al., *Cancer Res.*, 46:2068-2071 (1986).
Shoda et al., *Growth Factors*, 8:165-172 (1993.
Smith et al., *Brain Res.*, 543:111-122 (1991).
Smith et al., *Dev. Biol.*, 138:377-390 (1990).
Smith et al., *J. Neurochem.*, 60:1453-1466 (1993).
Sompayrac et al., *PNAS*, 78:7575-7578 (1981).
Song et al., *Mol. Biol. Cell*, 5:384a (1994) and 34th Ann. Mtg of the American Soc. for Cell Biol., San Francisco, CA (1994).
Sporn et al., *Nature*, 332:217-219 (1988).
Sporn et al., *Science*, 233:532-534 (1986).
Storm et al., *Nature*, 368:639-642 (1994).
Sugino et al., *J. Biol. Chem.*, 268:15579 (1993).
Suggs et al., *PNAS*, 78:6613-6617 (1981).
Sumitomo et al., *Biochem. Biophys. Acta.*, 208:1 (1995).
Sumitomo et al., *DNA Sequence-J. DNA Sequence and Mapping* 3:297-302 (1993).
Suzuki et al., *Proc Natl Acad Sci USA* 91:10255-59 (1994).
Tabas et al., *Genomics*, 9:283-289 (1991).
Takagi et al., *Clin. Orthopaed. Related Res.*, 171:224-231 (1982).
Taniguchi et al., *PNAS*, 77:5230-5233 (1980).
Tatusova et al., *FEMS Microbiol. Lett.*, 174:247-250 (1990).
Ten Dijke et al., *J. Biol. Chem.*, 269:16985-16988 (1994).
Ten Dijke et al., *EMBL* Z22534 (Apr. 6, 1993).
Ten Dijke et al., *EMBL Sequence Database, European Molecular Biology Laboratory* (Basel, CH), Accession No. Z22535 (1993).
Ten Dijke et al., *EMBL Sequence Database, European Molecular Biology Laboratory* (Basel, CH), Accession No. Z22536 (1993).
Thies et al., *J. Bone Min. Res.*, 5:305 (1990).
Thies et al., *Endocrinol.*, 130:1318-1324 (1992).
Thomsen et al., *Trends in Genetics*, 13:209-211 (1997).
Thomsen et al., *Cell*, 74:433-441 (1993).
Tona et al., *J. Histochem. Cytochem.*, 41:591-599 (1993).
Toriumi et al., *Arch. Otolaryngol. Head Neck Surg.*, 117:1101-1112 (1991).
Tsuchida et al., *PNAS*, 90:11242-11246 (1993).
Tsukazaki et al., *Calcif. Tissue Int.*, 57:196-200 (1995).
Tuszynski, *Cell Transplantation*, 9:629-636 (2000).
Ueno et al., *PNAS*, 84:8282-8286 (1987).
Ulrich et al., *EMBO J.*, 3:361-364 (1984).
Urdal et al., *PNAS*, 81:6481-6485 (1984).
Urist et al., *Fed. Proceed.*, Bethesda, MD, US, 3:746 (1985).
Urist et al., *PNAS*, 81:371-375 (1984).
Urist et al., *Clin Orthopaed. and Related Res.*, 187: 277-280 (1984).
Urist et al., *Proc. Soc. Exper. Biol. & Med.*, 2:194 (1983).
Urist et al., *Science*, 220:680-686 (1983).
Urist et al., *PNAS*, 70:3511 (1973).
Urist et al., *Clin. Orthoped. Rel. Res.*, 214:295-304 (1986).
Urlaub et al., *PNAS*, 77:4216-20 (1980).
Vukicevic et al. *PNAS*, 93:9021-6 (1996).
Wall et al., *J. Cell Biol.*, 120:493-502 (1993).
Wang et al., *Cell*, 67:797-805 (1991).
Wang et al., *J. Cell Biochem.*, Suppl. 15, Part E, p. 161, Abstract Q020 (1991).
Wang et al., *PNAS*, 87:2220-2224 (1990).
Wang et al., *PNAS*, 85:9484-9488 (1988).
Wang, E.A., *Trends in Biotech.*, 11:379-383 (1993).
Wang et al., *Cell*, 88:757-766 (1997).
Wang et al., *Stroke*, 32:2170-2178 (2001).
Weeks et al., *Cell*, 51:861-867 (1987).
Wells, *Biochemistry*, 29:8509-8517 (1990).
Wharton et al., *PNAS*, 88:9214-9218 (1991).
Wolpe et al., *FASEB J.*, 3:2565-2573 (1989).
Wolpe et al., *J. Biochem. Suppl. O*, Abstract H141, 13 Part C:21 (1989).
Wolpe et al., *J. Exp. Med.*, 167:570 (1988).
Wong et al., *Science*, 228:810-815 (1985).
Woo et al., *PNAS*, 75:3688-3691 (1978).
Wood et al., *PNAS*, 82:1585-1588 (1985).
Wozney et al., *J. Cell Sci.*, Suppl. 13:149-156 (1990).
Wozney, *Mol. Reproduction & Develop.*, 32:160-167 (1992).
Wozney et al., *Science*, 242:1528-1534 (1988).
Wozney, J.M., *Prog. Growth Factor Res.*, 1:267-280 (1989).
Wozney et al., *Handbook of Exp. Pharm.*, eds., G.R. Mundy and T.J. Martin; Springer-Verlag, Berlin, Chapter 20, 107:725-748 (1993).
Wozney, *Cell & Mol. Biol. Bone*, pp. 131-167 (1993) (Academic Press, Inc.).
Wozney et al., *J. Cell Biochem.*, Suppl. 16F:76 Abstract (1992).
Wozney *Spine*, 27:S2-S8 (2002).
Wright et al., *Leukemia Res.*, 4:537 (1980).
Wright et al., *Cell Tissue Kinet.*, 18:193 (1985).
Xu et al., *Proc Natl Acad Sci USA*, 91:7957-61 (1994).
Yamaguchi et al., *Nippon Rinsho*, 50:1932-1938 (1992).
Yamaji et al., *Biochem. Biophys. Res. Comm.*, 205:1944-1951 (1994).
Zipfel et al., *J. Immunol.*, 142:1582 (1989).
Zheng et al., *Path. Res. Pract.*, 188:1104-1121 (1992).

Zhou et al., *Nature*, 361:543-547 (1993).

Klein-Nulend et al., "Stimulation of Cartilage Differentiation by Osteogenic Protein-1 in Cultures of Human Perichondrium," *Tissue Engineering* 4(3):305-313 (1998).

Reddi, A. et al., "Bone Morphogenetic Proteins. Potential Role In Osteoporosis," *Osteoporosis, Academic Press Ch. 9*:281-287 (1996).

Takagi, et al., "The Role of Bone Marrow in Bone Morphogenetic Protein-Induced Repair of Femoral Massive Diaphyseal Defects," *Clinical Orthopaedics and Related Research* 171:224-231 (1982).

Wang, "Bone morphogenetic proteins (BMP): therapeutic potential in healing bony defects," *Trends in Biotechnology* 11:379-383 (1993).

Brown, Clin. Ortho. Related Res. 334:282-290 (1997).

Bugbee et al., Clin. Sports Med. 18:67-75 (1999).

Cook, Clin. Ortho. Related Res. 324:29-38 (1996).

Minutes of Oral Proceedings before the European Patent Office Opposition Division for EP 1148897.

Notice of Revocation of EP1148897.

Gao, Tissue Eng. 4:363-371 (2001).

Gilbert, Am. J. Knee Surg. 11:42-46 (1998).

Grgic et al., Acta Med. Croatica 51:23-27 (1997).

Hangody et al., Orthopedics 21:751-756 (1998).

Mow et al., J. Biomech. Eng. 113:198-207 (1991).

Sellers et al., J. Bone Joint Surg. 19A(10):1452-63 (1997).

Smith+Nephew technical Guide Mosaicplasty.

Tomford et al., Orthopaedics 15:1183-1188 (1992).

Vunjak-Novakovic, Orthod. Craniofacial Res. 8:209-218 (2005).

Wuisman, Z. Orthop. 133:166-175 (1995).

\* cited by examiner

METHODS AND COMPOSITIONS FOR HEALING AND REPAIR OF ARTICULAR CARTILAGE

This application is a continuation of application Ser. No. 09/493,545, filed Jan. 28, 2000 (U.S. Pat. No. 6,727,224), which claims priority from U.S. Ser. No. 60/118,160, filed Feb. 1, 1999, both of which are incorporated herein by reference.

FIELD OF THE INVENTION

The present invention relates to the field of tissue repair, specifically, the regeneration of stable and functional articular cartilage repair. Thus, the present invention may be useful in reconstructive surgery or other procedures for the regeneration or repair of articular cartilage.

BACKGROUND OF THE INVENTION

The repair of articular cartilage injuries remains a challenge in present day orthopedics. Several of the current therapeutic strategies are based upon the grafting of chondral and osteochondral tissues. Autologous osteochondral grafting provides the most appropriate physiological material. However, donor tissue is limited, and often requires surgery at a secondary site in order to harvest tissue for transplant. Accordingly, despite substantial endeavors in this field, there remains a need for an effective method of repair of articular cartilage defects and injuries which provides appropriate physiological repair without the need to collect autologous tissue from the patient.

SUMMARY OF THE INVENTION

The present invention provides methods and compositions for regenerating functional and physiologically appropriate tissue repair for the repair of articular cartilage injuries and defects. In particular, the present invention comprises methods of treating patients with articular cartilage injuries or defects. The methods and compositions of the present invention are advantageous in that they utilize bone morphogenetic proteins (BMPs), which are known to have osteogenic and/or chondrogenic properties, and which may be produced via recombinant DNA technology, and therefore are of potentially unlimited supply. The methods and compositions of the present invention are further advantageous in that regeneration of functional articular cartilage may be accelerated or may be of greater ultimate strength and stability, and the tissue formed at the site of the defect or injury is physiologically appropriate.

The use of BMP to augment the repair of articular cartilage defects and injuries may result in better methods for treatment of osteoarthritis, thus obviating, delaying or reducing the need for artificial hip replacements and other common interventions. Preclinical evaluations indicate that rhBMP-2 improves early healing of full thickness defects of articular cartilage in rabbits.

DETAILED DESCRIPTION OF THE INVENTION

According to the present invention, methods and compositions are provided for treatment of patients who suffer from some form of articular cartilage injury or defect. The injury may be the result of acute stress, or injury, such as resulting from participation in athletics, or from accidental occurrences which tear, mar or otherwise injure the articular cartilage.

The methods and composition are advantageous in that repair or improvement of articular cartilage defects, particularly full thickness articular cartilage defects. Other defects may also be treated by the methods and compositions of the present invention, particularly with an additional procedure in which the site of the defect is further aggravated so as to reach the underlying subchondral bone.

In the present invention, active growth factor, such as a BMP, is added to a suitable tissue source. The tissue source may be an osteochondral graft, either autologous to the patient, or may comprise allograft or artificially prepared tissue. In a preferred embodiment, the tissue source may be chondrocytic cell cultures, such as chondrocyte or stem cell cultures which have been prepared through ex vivo cell culture methods, with or without additional growth factors. For example, see the disclosure of U.S. Pat. No. 5,226,914; U.S. Pat. No. 5,811,094; U.S. Pat. No. 5,053,050; U.S. Pat. No. 5,486,359; U.S. Pat. No. 5,786,217 and U.S. Pat. No. 5,723,331. The disclosures of all of these applications are hereby incorporated herein by reference.

The tissue may also be harvested by traditional non-cell culture based means, using techniques such as mosaicplasty, in which cartilage is harvested using commercially available instruments such as Acufex7 [Smith and Nephew, Inc., Andover MA]; COR System [Innovasive Technologies, Marlborough MA]; or Arthrex7 Osteochondral Autograft Transfer System [Arthrex, Munich, Germany]. The tissue harvested may be applied directly in the methods of the present invention, or may be combined with the tissue based cell culture systems described above.

GROWTH FACTOR

The active growth factor used in the present invention is preferably from the subclass of proteins known generally as bone morphogenetic proteins (BMPs), which have been disclosed to have osteogenic, chondrogenic and other growth and differentiation type activities. These BMPs include rhBMP-2, rhBMP-3, rhBMP-4 (also referred to as rhBMP-2B), rhBMP-5, rhBMP-6, rhBMP-7 (rhOP-1), rhBMP-8, rhBMP-9, rhBMP-12, rhBMP-13, rhBMP-15, rhBMP-16, rhBMP-17, rhBMP-18, rhGDF-1, rhGDF-3, rhGDF-5, rhGDF-6, rhGDF-7, rhGDF-8, rhGDF-9, rhGDF-10, rhGDF-11, rhGDF-12, rhGDF-14. For example, BMP-2, BMP-3, BMP4, BMP-5, BMP-6 and BMP-7, disclosed in U.S. Pat. Nos. 5,108,922; 5,013,649; 5,116,738; 5,106,748; 5,187,076; and U.S. Pat. No. 5,141,905; BMP-8, disclosed in PCT publication WO91/18098; and BMP-9, disclosed in PCT publication WO93/00432, BMP-10, disclosed in U.S. Pat. No. 5,637,480; BMP-11, disclosed in U.S. Pat. No. 5,639,638, or BMP-12 or BMP-13, disclosed in U.S. Pat. No. 5,658,882, BMP-15, disclosed U.S. Pat. No. 5,635,372 and BMP-16, disclosed in co-pending patent application Ser. No. 08/715,202. Other compositions which may also be useful include Vgr-2, and any of the growth and differentiation factors [GDFs], including those described in PCT applications WO94/15965; WO94/15949; WO95/01801; WO95/01802; WO94/21681; WO94/15966; WO95/10539; WO96/01845; WO96/02559 and others. Also useful in the present invention may be BIP, disclosed in WO94/01557; HP00269, disclosed in JP Publication number: 7-250688; and MP52, disclosed in PCT application WO93/16099. The disclosures of all of these applications are hereby incorporated herein by reference. Also useful in the present invention are heterodimers of the above and modified proteins or partial deletion products thereof. These proteins can be used individually or in mixtures of two or more, and rhBMP-2 is preferred.

The BMP may be recombinantly produced, or purified from a protein composition. The BMP may be homodimeric, or may be heterodimeric with other BMPs (e.g., a heterodimer composed of one monomer each of BMP-2 and BMP-6) or with other members of the TGF-β superfamily, such as activins, inhibins and TGF-β1 (e.g., a heterodimer composed of one monomer each of a BMP and a related member of the TGF-β superfamily). Examples of such heterodimeric proteins are described for example in Published PCT Patent Application WO 93/09229, the specification of which is hereby. incorporated herein by reference. The amount of osteogenic protein useful herein is that amount effective to stimulate increased osteogenic activity of infiltrating progenitor cells, and will depend upon the size and nature of the defect being treated, as well as the carrier being employed. Generally, the amount of protein to be delivered is in a range of from about 0.05 to about 1.5 mg.

In a preferred embodiment, the osteogenic protein is administered together with an effective amount of a protein which is able to induce the formation of tendon- or ligament-like tissue. Such proteins, include BMP-12, BMP-13, and other members of the BMP-12 subfamily, as well as MP52. These proteins and their use for regeneration of tendon and ligament-like tissue are disclosed in U.S. application Ser. No. 08/362,670, filed on Dec. 22, 1994, the disclosure of which is hereby incorporated herein by reference. In another preferred embodiment, a heterodimer in which one monomer unit is an osteogenic protein such as BMP-2, and the other monomer subunit is a tendon-inducing protein, such as BMP-12, is administered in accordance with the methods described below, in order to induce the formation of a functional attachment between connective tissue and bone.

APPLICATION OF GROWTH FACTOR

Growth factor may be applied to the tissue source in the form of a buffer solution. One preferred buffer solution is a composition comprising, in addition to the active growth factor, about 1.0 to about 10.0% (w/v) glycine, about 0.1 to about 5.0% (w/v) of a sugar, preferably sucrose, about 1 to about 20 mM glutamic acid hydrochloride, and optionally about 0.01 to about 0.1% of a non-ionic surfactant, such as polysorbate 80. Preferred solutions are from about 1% to about 20% w/v cellulosic carrier/buffer. If desired, a salt may be added.

Other materials which may be suitable for use in application of the growth factors in the methods and compositions of the present invention include hyaluronic acid, surgical mesh or sutures, polyglyconate, temperature-sensitive polymers, demineralized bone, minerals and ceramics, such as calcium phosphates, hydroxyapatite, etc., as well as combinations of the above described materials. In the preferred embodiment of the present invention, however, no carrier is employed.

The growth factor of the present invention, in a suitable buffer such as that described above, or combined with a suitable carrier, may be applied directly to the tissue and/or to the site in need of tissue repair. For example, the growth factor may be physically applied to the tissue through spraying or dipping, or using a brush or other suitable applicator, such as a syringe for injection. Alternatively, or in conjunction, the protein may be directly applied to the site in need of tissue repair.

The following examples further describe the practice of embodiments of the invention with BMP-2. The examples are not limiting, and as will be appreciated by those skilled in the art, can be varied in accordance with the above specification.

EXAMPLES

I. Rabbit Allograft

All procedures were carried out with approval from IACUC. Twelve male New Zealand white rabbits (6 months old) were used. Two rabbits served as donors and 10 as recipients. Osteochondral grafts (3.5 mm diameter) were harvested from the trochlear groove or the medial femoral condyle of the donors, and transplanted into a 3.5 mm deep defect in the trochlear groove of the recipient. The graft was bathed in either rhBMP-2 (0.5 mg/ml) or buffer control prior to implantation. The rabbits were sacrificed 4 weeks after surgery and the transplants and surrounding tissue were evaluated by a histologic-histochemical grading scale, as described in Sellers et al., *J. Bone Joint Sure.*, 79-A: 1452-1463 (1997). Computerized image analysis of histologic sections was also performed. Results were evaluated using the unpaired Students t-test.

On gross examination, the joints showed no signs of inflammation. All the defects were filled by repair tissue. The surface appearance of the defects was variable but acceptable and did not correlate with form of treatment. Osteophytes were found in 3 joints (2 in the experimental group; 1 in control buffer group).

There was no correlation between the gross and histologic appearance in any of the defects. The presence of chondrocytes in the lacunae and sporadic cloning of cells in the donor cartilage indicated survival of the tissue. Focal degeneration of the donor cartilage was present in all of the control groups, but only one of the rhBMP-2 treated group. The healing of the defect in the rhBMP-2 treated group was significantly improved compared to that in the control group. The rhBMP-2 treated group had improved bony integration indicated by less fibrous repair tissue in the subchondral bone compartment. Treatment with rhBMP-2 also resulted in more cartilage above the original tidemark, apparently consisting of both donor tissue and newly regenerated recipient cartilage. There was no significant difference in the total amount of bone observed between the two groups.

TABLE I

HISTOLOGIC SCORE AND HISTOMORPHOMETRIC MEASUREMENT FOR CARTILAGE REPAIR, MEAN VALUE (SD)

| Parameter | rhBMP-2 | Control |
|---|---|---|
| Average Score** | 10.0 (5.42)* | 20.6 (5.18) |
| % of bone under tidemark | 73.26 (13.28) | 62.88 (18.07) |
| % of fibrous tissue under tidemark | 2.19 (2.04)* | 15.81 (9.88) |
| % of cartilage above tidemark | 74.70 (41.08)* | 18.17 (26.70) |
| % of filing of the defect | 96.53 (4.86)* | 88.79 (8.04) |

*Statistically significant difference from control ($p < 0.05$).
**Scale system ranges from 0 (normal cartilage) to 31 (no repair).

Additional histomorphometric analysis data further supports the beneficial effects of rhBMP-2 on the healing of graft. For example, the percentage filling of the new tissue above tide marker has been shown to be 81.52% in a rhBMP-2 treated group vs. 57.63% in control. There was less graft cartilage degeneration in rhBMP-2 treated group (23.83%) than in control group (44.52%). The integration of the graft or newly formed cartilage with the host cartilage was improved by rhBMP-2 treatment (56.48%) compared to that of control group (21.89%). More new cartilage formed under the influence of rhBMP-2 either at the edge of graft, which eliminated the gap between the graft and host, or at the top of graft, which made the graft more congruent with the joint surface.

The above results demonstrate that the healing of allogeneic osteochondral grafts in articular cartilage defects was improved by the addition of rhBMP-2. The active growth factor may have accelerated subchondral bone union, providing support and nutrition to the articular cartilage tissue. Addition of growth factor may also have stimulated new cartilage formation from recipient mesenchymal stem cells in the bone marrow and/or the synovial tissue. These results suggest that the combination of active growth factor, particularly the bone morphogenetic proteins, and osteochondral allografts might present a potent strategy for treatment of articular cartilage defects, particularly full thickness articular cartilage defects.

II. Rabbit Autograft

Osteochondral grafts (2.7 mm in diameter and 3.0 mm long) were harvested from the trochlear groove or femoral condyle and transplanted into a donor site 2.7 mm wide and 3.5 mm long on the trochlear groove or femoral condyle of the knee joint in rabbits. Half the animals had buffer dripped into the recipient site prior to transplantation, and then the grafts were dipped in buffer for 2 minutes and placed into the recipient site. The other half had 5 µg rhBMP-2 dripped into the recipient site prior to transplantation, and then the graft was dipped into buffer containing 500 µg/ml rhBMP-2 for 2 minutes and then transplanted into the recipient site. The animals were sacrificed 4 weeks after surgery, and the recipient sites were evaluated histologically using both a histologic-histochemical grading scale [Sellers, et al., J. Bone Joint Surg., 79-A: 1452-63 (1997)] and quantitative computerized image analysis of the tissue. The data indicated that treatment with rhBMP-2 improved the healing of the autograft. The most dramatic effects were the reduction of graft cartilage degeneration (rhBMP-28.18% vs. control 36.25%), and more cartilage formed at the edge of graft (rhBMP-288.23% vs. control 50%).)

III. Non-Human Primate Autograft:

The non human primates used for autografts experiments were cynomologous macaques. Osteochondral grafts (3.5 mm diameter×6 mm long) were harvested from the trochlear groove of 6 cynomologous macaques and transplanted into recipient sites drilled into both the medial and lateral femoral condyle of the same animal (n=12 transplants total). Prior to transplantation 25 µg rhBMP-2 was dripped into 6 recipient sites, and the grafts from those 6 transplants were dipped into a solution of 1.25 mg/ml rhBMP-2 for 2 minutes. In the other 6 transplants, buffer alone was dripped into the recipient sites and the grafts were dipped into buffer alone for 2 minutes prior to transplantation. The limbs were immobilized in a cast for 2 weeks post-operatively, and the animals were sacrificed 9 weeks post operatively.

All the animals had normal function of their knee joints. On gross examination, the joints showed no signs of inflammation. Osteophytes were not found in any joint. Although the surface of the defects appeared level with the surrounding cartilage on gross examination, microscopic observation revealed subsidence of the grafts in most of the cases. The tissue observed grossly covering the surface was actually new-formed tissue on the top of graft. Computerized image analysis was performed by a blinded evaluator to quantitate percent filling of the defect, the new tissue types formed above the original tide mark, and the integration of the grafts and the surrounding cartilage. Favorable results were observed in the rhBMP-2 treated group in all these parameters. More new cartilage formed between the graft and host cartilage to eliminate the gap resulting in better integration of the graft with the surrounding cartilage (rhBMP-2 88.59% vs. control 64.82%). The filling of the cartilage defect was better in rhBMP-2 treated group (95.02%) than in the control group (86.68%). There was more fibrous tissue in the control group (11.90% vs. rhBMP-2 5.65%), while more transitional tissue was found in the rhBMP-2 treated group (36.38% vs. control 20.53%). There was no significant difference on the overall histologic-histochemical score between the two groups. Peripheral quantitative computed tomography (pQCT) showed that the bone density increased in the donor sites with time. At 6 weeks and 9 weeks after the operation, the tissue in the rhBMP-2 treated donor sites was significantly denser and the healing process was more advanced compared to control sites. Histologically, the donor sites contained regenerated bone trabeculae with fibrous tissue at the surface in all the cases.

IV. rhBMP-2 Retention Ex Vivo:

Retention of rhBMP-2 in osteochondral graft with this technique was evaluated with the grafts from non-human primates. The graft was dipped in a mixture solution of $^{125}$I labeled rhBMP-2 and unlabeled rhBMP-2. Results showed that the amount of rhBMP-2 absorbed to graft was proportional to the concentration of the protein, and the time of soaking. Other factors, which affect the retention of rhBMP-2, included the size of graft, and the presence of marrow elements between trabecular bone.

V. rhBMP-2 Retention Time Course In Vivo:

The time course of rhBMP-2 retention in osteochondral graft was evaluated in rabbits. A mixture solution of $^{125}$I labeled rhBMP-2 and unlabeled rhBMP-2, which contained 5 ug rhBMP-2 and 20 uCi $^{125}$I, was loaded to the graft before implantation. The animals were scanned with y-camera during the follow-up time for 22 days post-operatively. Compared to the time course of collagen sponge as a carrier, the half time of rhBMP-2 in osteochondral graft was increased from 1 day to 3 days. The radioactivity of 10% of the starting point was maintained from 11 days of collagen sponge to 22 days of graft.

VI. Non-Human Primate Allografts:

Donor sites (3.5 mm wide×6 mm long) were removed from the trochlear grooves of 12 adult cynomologous macaques and transplanted into 3.5×6 mm recipient sites in the medial and lateral femoral condyles of unrelated individuals. Half of the transplants were soaked in 1.25 mg/ml rhBMP-2 for 2 minutes prior to transplantation, and half were soaked in buffer. The identical procedure was performed on the other limb 7 weeks after the first surgery. The limb was immobilized in a cast for 2 weeks post operatively after each surgery, and the animals were sacrificed 9 weeks after the second surgery for histologic analysis.

These results suggest that the combination of active growth factor, particularly the bone morphogenetic proteins, and osteochondral autografts might present a potent strategy for treatment of articular cartilage defects, particularly full thickness articular cartilage defects.

In other embodiments BMP-2 may also be applied to frozen osteochondral allograft for treatment of focal articular cartilage defect.

The foregoing descriptions detail presently preferred embodiments of the present invention. Numerous modifications and variations in practice thereof are expected to occur to those skilled in the art upon consideration of these descriptions. Those modifications and variations are believed to be encompassed within the claims appended hereto.

We claim:

1. A method for regeneration of articular cartilage comprising administering to an area in need of regeneration of said articular cartilage an osteochondral graft having applied thereto a composition consisting essentially of an amount of a heterodimer effective for the regeneration of articular cartilage, wherein the heterodimer comprises one purified bone morphogenetic protein (BMP) selected from the group consisting of BMP-2, 4, 5, 6, and 7 and one protein which induces the formation of tendon or ligament tissue selected from the group consisting of BMP-12, BMP-13, and MP52.

2. The method of claim 1, wherein said BMP is BMP-2.

3. A method for regeneration of articular cartilage comprising administering to an area in need of regeneration of said articular cartilage an osteochondral graft having applied thereto a composition consisting essentially of
   (i) an amount of at least one purified bone morphogenetic protein (BMP) selected from the group consisting of BMP-2, 4, 5, 6, and 7 effective for the regeneration of said articular cartilage and
   (ii) one or more pharmaceutical carriers.

4. The method of claim 3, wherein said pharmaceutical carrier is hyaluronic acid.

5. The method of claim 3, wherein the pharmaceutical carrier is a mineral.

6. The method of claim 5, wherein said mineral is calcium phosphate.

7. The method of claim 3, wherein said pharmaceutical carrier is a ceramic.

8. The method of claim 7, wherein said ceramic is hydroxyapatite.

9. A method for regeneration of articular cartilage comprising administering to an area in need of regeneration of said articular cartilage an osteochondral graft and a composition consisting essentially of an amount of at least one purified bone mor ho enetic protein (BMP) selected from the group consisting of BMP-2, 4, 5, 6, and 7 effective for the regeneration of said articular cartilage, wherein said composition is applied directly to the osteochondral graft and/or administered directly to the site in need of tissue repair in conjunction with the graft.

10. The method of claim 9, wherein said composition is applied to the graft or the site in need of tissue repair using a syringe for injection.

11. A method for regeneration of articular cartilage comprising administering to an area in need of regeneration of said articular cartilage an osteochondral graft having applied thereto a composition consisting essentially of an amount of at least one purified bone morphogenetic protein (BMP) selected from the group consisting of BMP-2, 4, 5, 6, and 7 effective for the regeneration of said articular cartilage, wherein the area in need of regeneration of said articular cartilage is selected from the group consisting of the hip and the knee.

12. The method of claim 11, wherein the area in need of regeneration of said articular cartilage is the hip.

13. The method of claim 11, wherein the area in need of regeneration of said articular cartilage is the knee.

14. The method of claim 13, wherein the area in need of regeneration of articular cartilage is the trochlear groove.

15. The method of claim 13, wherein the area in need of regeneration of articular cartilage is the femoral condyle.

16. The method of claim 15, wherein the area in need of regeneration of articular cartilage is the medial femoral condyle.

17. The method of claim 15, wherein the area in need of regeneration of articular cartilage is the lateral femoral condyle.

18. The method of claim 3, wherein the BMP is BMP-2.

* * * * *

UNITED STATES PATENT AND TRADEMARK OFFICE
CERTIFICATE OF CORRECTION

| | | |
|---|---|---|
| PATENT NO. | : 7,323,445 B2 | Page 1 of 1 |
| APPLICATION NO. | : 10/779638 | |
| DATED | : January 29, 2008 | |
| INVENTOR(S) | : Renwen Zhang, Diane Peluso and Elisabeth Morris | |

It is certified that error appears in the above-identified patent and that said Letters Patent is hereby corrected as shown below:

IN THE CLAIMS:

In claim 9, column 8, line 3, change "mor ho enetic" to --morphogenetic--

Signed and Sealed this

Sixth Day of May, 2008

JON W. DUDAS
*Director of the United States Patent and Trademark Office*